United States Patent [19]

Acker et al.

[11] Patent Number: 4,579,842
[45] Date of Patent: Apr. 1, 1986

[54] ORGANOSILYL COMPOUNDS AND THEIR USE AS FUNGICIDES

[75] Inventors: Rolf-Dieter Acker, Leimen; Ernst Buschmann, Ludwigshafen; Ernst-Heinrich Pommer, Limburgerhof; Eberhard Ammermann, Ludwigshafen, all of Fed. Rep. of Germany

[73] Assignee: BASF Aktiengesellschaft, Fed. Rep. of Germany

[21] Appl. No.: 695,687

[22] Filed: Jan. 28, 1985

Related U.S. Application Data

[62] Division of Ser. No. 487,313, Apr. 21, 1983.

[30] Foreign Application Priority Data

Apr. 24, 1982 [DE] Fed. Rep. of Germany ....... 3215409

[51] Int. Cl.$^4$ .............................................. A01N 55/00
[52] U.S. Cl. .................................................... 514/63
[58] Field of Search .......................... 424/184; 514/63

[56] References Cited

U.S. PATENT DOCUMENTS

| | | | |
|---|---|---|---|
| 3,505,376 | 4/1970 | Frankel et al. ................... | 260/448.2 |
| 3,558,683 | 1/1971 | Belsky et al. ..................... | 260/448.2 |
| 3,692,798 | 9/1972 | Barcza ............................. | 424/184 |

FOREIGN PATENT DOCUMENTS

| | | |
|---|---|---|
| 988630 | 3/1965 | United Kingdom . |
| 1525300 | 9/1978 | United Kingdom . |

*Primary Examiner*—Allen J. Robinson
*Attorney, Agent, or Firm*—Keil & Weinkauf

[57] ABSTRACT

Organosilyl compounds of the general formula I

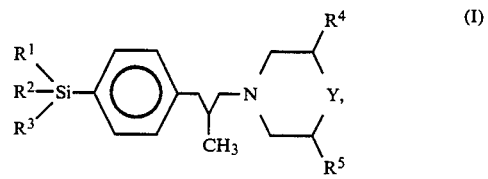

where $R^1$, $R^2$ and $R^3$ are alkyl, substituted alkyl, alkenyl, alkynyl, cycloalkyl, phenyl or substituted aryl, $R^4$ and $R^5$ are alkyl or hydrogen and Y is $CH_2$, oxygen, nitrogen or alkyl-substituted nitrogen, their salts and fungicides containing these compounds.

5 Claims, No Drawings

ORGANOSILYL COMPOUNDS AND THEIR USE AS FUNGICIDES

This application is a division of U.S. application Ser. No. 487,313, filed Apr. 21, 1983, which is on appeal to the Board of Appeals.

The present invention relates to novel organosilyl compounds, fungicides containing these as active ingredients, processes for the preparation of such fungicidal mixtures and methods of controlling harmful fungi using these fungicides.

German Pat. Nos. 1,164,152 and 1,173,722, and German Laid-Open Application DOS No. 2,641,513 disclose the use of N-tridecyl-2,6-dimethylmorpholine and its salts, eg. its acetate and dodecylbenzenesulfonate, as fungicides.

We have found that organosilyl compounds of the formula I

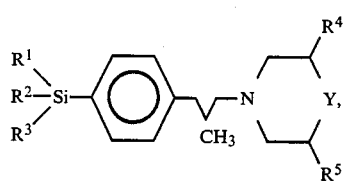

where $R^1$, $R^2$ and $R^3$ are identical or different and each is $C_1$–$C_{10}$-alkyl, substituted $C_1$–$C_{10}$-alkyl, alkenyl, alkynyl, $C_3$–$C_8$-cycloalkyl, phenyl or substituted aryl, $R^4$ and $R^5$ are identical or different and each is $C_1$–$C_5$-alkyl or hydrogen and Y is $CH_2$, oxygen, nitrogen or alkyl-substituted nitrogen, and their salts, have a very good fungicidal activity.

Examples of $C_1$–$C_{10}$-alkyl radicals are $C_1$–$C_4$-alkyl, eg. methyl, ethyl, butyl and pentyl, and hexyl and decyl. Substituted $C_1$–$C_{10}$-alkyl radicals are substituted by, for example, halogen, such as chlorine or bromine, alkoxy, such as methoxy or ethoxy, or dialkylamino, such as dimethylamino, and examples are halogeno-$C_1$–$C_4$-alkyl, such as chloromethyl, bromo-i-propyl, dichloroethyl, tribromobutyl and fluoroethyl, and cyanononyl and methylthiomethyl.

Examples of alkenyl radicals are $C_2$–$C_4$-alkenyl radicals, for example allyl, vinyl and methallyl, and substituted alkenyl radicals, eg. chloroallyl and methoxyallyl.

Examples of alkynyl radicals are $C_2$–$C_4$-alkynyl, such as propargyl and ethynyl.

Examples of $C_3$–$C_8$-cycloalkyl radicals are cyclopropyl, cyclohexyl, cyclopentyl, cyclooctyl, methylcyclohexyl and dimethylcyclohexyl.

Examples of substituted aryl radicals are halophenyls, such as dichlorophenyl and fluorophenyl, and methoxyphenyl, tolyl, t-butylphenyl, methylthiophenyl and dimethylaminophenyl.

Examples of $C_1$–$C_5$-alkyl radicals are methyl, ethyl, i-propyl and n-pentyl.

Examples of alkyl-substituted nitrogen are $C_1$–$C_2$-alkyl-substituted nitrogen, such as N-methyl and N-ethyl.

Preferred organosilyl compounds of the formula I are those where $R^1$, $R^2$ and $R^3$ are each $C_1$–$C_4$-alkyl or chloro-$C_1$–$C_4$-alkyl, $R^4$ and $R^5$ are each methyl or hydrogen and Y is $CH_2$ or oxygen.

The novel compounds of the formula I can be prepared by reacting a compound of the formula II

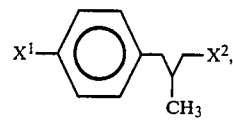

where $X^1$ and $X^2$ are identical or different and each is halogen, with an alkali metal or alkaline earth metal or an organometallic compound containing an alkali metal or alkaline earth metal, $X^1$ being replaced by an alkali metal or alkaline earth metal, and reacting the resulting metal compound with a halosilane of the formula III

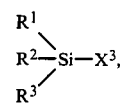

where $R^1$, $R^2$ and $R^3$ have the above meanings and $X^3$ is halogen, and reacting the resulting compound of the formula IV

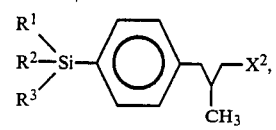

where $R^1$, $R^2$, $R^3$ and $X^2$ have the above meanings, with a heterocyclic amine of the formula V

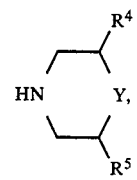

where $R^4$, $R^5$ and Y have the above meanings, if necessary together with an auxiliary base.

The reaction with the metal compounds is carried out at, for example, from $-80°$ to $+60°$ C., preferably with a metal such as lithium, sodium, potassium, magnesium or calcium. Suitable organometallic compounds are organic derivatives of these metals, especially alkyl-lithium compounds, such as methyl-lithium, n-, sec.- or t-butyl-lithium and phenyl-lithium, or alkyl-magnesium halides, eg. methyl-magnesium chloride or ethyl-magnesium bromide, and metal-alkylamines, eg. lithium-diisopropylamine. The chlorosilane III is added at, for example, from $-40°$ to $+30°$ C., and the mixture may be subsequently stirred at a higher temperature in order to bring the reaction to completion. The compound of the formula IV can then be either used directly for the next reaction or purified in a conventional manner, for example by distillation or chromatography.

The compound of the formula IV is reacted with the compound of the formula V at, for example, from 50° to 150° C., the reaction requiring from 2 to 12 hours. If necessary, an auxiliary base may be added to bond the acid formed. The compound I can be purified in a conventional manner, for example by extraction, crystallization, distillation or chromatography. From 0.5 to 1.5 equivalents of the metal or organometallic compound, from 0.8 to 1.5 equivalents of the chlorosilane III, from 1.0 to 5.0 equivalents of the compound V and, if necessary, from 0.8 to 1.5 equivalents of the auxiliary base are used, for example, per equivalent of the compound of the formula II.

Solvents or diluents which are inert under the particular reaction conditions are advantageously used. Examples of suitable solvents for the reaction with the metal compounds are ethers, such as diethyl ether, ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, ethylene glycol dimethyl ether, tetrahydrofuran and dioxane, and aliphatic, cycloaliphatic or aromatic hydrocarbons, such as hexane, pentane, heptane, pinane, nonane, o-, m- or p-cymene, gasoline fractions within the boiling point range from 70° to 190° C., cyclohexane, methylcyclohexane, decalin, petroleum ether, naphtha, toluene, o-, m- or p-xylene, 2,2,4-trimethylpentane, 2,2,3-trimethylpentane, 2,3,3-trimethylpentane and octane. Advantageously, from 100 to 2,000% by weight, preferably from 200 to 700% by weight, based on the starting substance II, of the solvent is used. Examples of suitable solvents for the reaction with compounds of the formula V are halohydrocarbons, in particular chlorohydrocarbons, such as tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- or p-difluorobenzene, 1,2-dichloroethane, 1,1-dichloroethane, 1,2-cis-dichloroethylene, chlorobenzene, fluorobenzene, bromobenzene, iodobenzene, o-, m- or p-dichlorobenzene, o-, m- or p-dibromobenzene, o-, m- or p-chlorotoluene and 1,2,4-trichlorobenzene, ethers, such as ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and β,β'-dichlorodiethyl ether, nitrohydrocarbons, such as nitromethane, nitroethane, nitrobenzene, o-, m- or p-chloronitrobenzene and o-nitrotoluene, nitriles such as acetonitrile, butyronitrile, isobutyronitrile, benzonitrile, or m-chlorobenzonitrile, aliphatic, cycloaliphatic or aromatic hydrocarbons, such as heptane, pinane, nonane, o-, m- or p-cymene, gasoline fractions having a boiling point range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane, esters, such as ethyl acetate, ethyl acetoacetate and isobutyl acetate, amides, such as formamide, methylformamide and dimethylformamide, and ketones, such as acetone and methyl ethyl ketone, and where relevant also water and appropriate mixtures. It is also possible to use an excess of the compound of the formula V as the solvent. Advantageously, from 100 to 2,000% by weight, preferably from 200 to 700% by weight, based on the starting substance II, of the solvent is used.

The auxiliary base used for the reaction with the compounds of the formula V may be any of the conventional acid acceptors, preferably a tertiary amine, an alkaline earth metal compound, an ammonium compound or an alkali metal compound or an appropriate mixture. Zinc compounds may also be used. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyl-toluidine, N,N-dimethyl-p-aminopyridine, N,N-diethyl-p-aminopyridine, N,N-dipropyl-p-aminopyridine, N-methyl-pyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrmidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

Advantageously, not more than 20% more or less than the equivalent amount, based on the starting substance II or IV, of the acid acceptor is used.

All the organic and inorganic acids which form phytophysiologically acceptable salts are suitable for salt formation with compounds of the formula I. Examples of salts are chlorides, bromides, iodides, sulfates, phosphates, acetates, oxalates, fumarates, malonates, alkylsulfonates and arylsulfonates.

The salts are obtained by mixing the corresponding acid with the free amine of the formula I, if necessary in an inert solvent, distilling off the solvent and recrystallizing the residue if necessary.

In the Examples which follow and which illustrate the preparation of the novel compounds, parts are by weight.

EXAMPLE 1

(a) a solution of 24.7 parts of 2-methyl-3-(4-bromophenyl)-propyl chloride in 20 parts of tetrahydrofuran (THF) were added dropwise to 2.4 parts of magnesium in 25 parts of THF. The reaction was maintained at from 50° to 52° C., and the mixture was then refluxed for a further 30 minutes. 16.5 parts of triethylchlorosilane were added dropwise at room temperature and the mixture was then refluxed again for 6 hours, cooled and filtered. The solution was concentrated and the residue was distilled to give, at a boiling point of 115°–120° C./0.01 mm Hg, 20.3 parts of 2-methyl-3-(4-triethylsilylphenyl)-propyl chloride of $n^{24}$ 1.5080.

(b) 13.5 parts of 2-methyl-3-(4-triethylsilylphenyl)-propyl chloride and 16.5 parts of cis-2,6-dimethylmorpholine were mixed and the mixture was stirred at 150° C. for 6 hours, cooled and brought to about pH 9 with saturated $Na_2CO_3$ solution. After extraction with methylene chloride, the organic phase was dried and concentrated and the residue was distilled to give, at a boiling point of 110°–114° C./0.01 mm Hg, 12.6 parts of 4-[3-(4-triethylsilylphenyl)-2-methylpropyl]-cis-2,6-dimethylmorpholine of $n_D^{23}$ 1.5025 (Compound No. 15).

RECIPE 1

10.0 parts of 2-methyl-3-(4-bromophenyl)-propyl chloride were introduced into 80 parts of THF, and a solution of 2.55 parts of n-butyl-lithium in pentane was then added dropwise at from −75° to −70° C. The mixture was then stirred at −50° C. for 30 minutes and 6.6 parts of n-butyldimethylchlorosilane were added dropwise at this temperature. The reaction mixture was subsequently stirred at −50° C. for 30 minutes and then allowed to warm to room temperature, and stirring was continued for 12 hours.

The mixture was filtered, the solvent was distilled off and the residue was distilled to give, at a boiling point of 96°–100° C./0.08 mbar, 9.8 parts of 2-methyl-3-(4-n-butyldimethylsilylphenyl)-propyl chloride of $n_D^{22}$ 1.5033.

RECIPE 1

15 parts of 2-methyl-3-(4-bromophenyl)-propyl chloride and 28 parts of cis-2,6-dimethylmorpholine were stirred at 150° C. for 8 hours. The reaction mixture was cooled, poured into 100 parts of water, brought to pH 9–10 with saturated aqueous $Na_2CO_3$ solution and extracted with methylene chloride. The organic phase was dried and concentrated and the residue was distilled to give, at a boiling point of 100°–102° C./0.01 mbar, 15.8 parts of 4-[3-(4-bromophenyl)-2-methylpropyl]-cis-2,6-dimethylmorpholine of $n_D^{22}$ 1.5265.

EXAMPLE 2

5.0 parts of 4-[3-(4-(n)-butyldimethylsilylphenyl)-2-methylpropyl]-cis-2,6-dimethylmorpholine and 7.6 parts of 20% strength aqueous hydrochloric acid were mixed and the mixture was stirred for 10 minutes. The precipitate was filtered off with suction, washed with cyclohexane and dried to give 4.9 parts of 4-[3-(4-(n)-butyldimethylsilylphenyl)-2-methylpropyl]-cis-2,6-dimethylmorpholine hydrochloride of melting point 159°–162° C. (Compound No. 25).

The following compounds were prepared in a similar manner:

| No. | $R^1$ | $R^2$ | $R^3$ | $R^4$ | $R^5$ | Y | salt | $n_D$/M.p./B.p. |
|---|---|---|---|---|---|---|---|---|
| 1 | $CH_3$ | $CH_3$ | $CH_3$ | H | H | $CH_2$ | — | 115-120° C./0.07 mbar |
| 2 | $CH_3$ | $CH_3$ | $CH_3$ | H | H | $CH_2$ | HCl | 152-154 |
| 4 | $CH_3$ | $CH_3$ | $CH_3$ | $CH_3$ | $CH_3$ | O | — | 145-147° C./0.07 mbar |
| 15 | $C_2H_5$ | $C_2H_5$ | $C_2H_5$ | $CH_3$ | $CH_3$ | O | — | 1.5025 |
| 22 | $n-C_4H_9$ | $CH_3$ | $CH_3$ | $CH_3$ | $CH_3$ | O | — | 1.4950 |
| 25 | $n-C_4H_9$ | $CH_3$ | $CH_3$ | $CH_3$ | $CH_3$ | O | HCl | 159-162° C. |
| 31 | $CH_2Cl$ | $CH_3$ | $CH_3$ | $CH_3$ | $CH_3$ | O | — | 1.5140 |
| 38 | $C_6H_5$ | $CH_3$ | $CH_3$ | H | H | $CH_2$ | — | 1.5475 |
| 39 | $C_6H_5$ | $CH_3$ | $CH_3$ | H | H | $CH_2$ | HCl | 197-200° C. |
| 40 | $C_6H_5$ | $CH_3$ | $CH_3$ | $CH_3$ | $CH_3$ | O | — | 1.5370 |
| 41 | $C_6H_5$ | $CH_3$ | $CH_3$ | $CH_3$ | $CH_3$ | O | HCl | viscous |
| 43 | $C_6H_5$ | $CH_3$ | $CH_3$ | H | H | O | — | 1.5503 |

The following compounds may be prepared analogously:

| No. | $R^1$ | $R^2$ | $R^3$ | $R^4$ | $R^5$ | Y | salt |
|---|---|---|---|---|---|---|---|
| 3 | $CH_3$ | $CH_3$ | $CH_3$ | H | H | $CH_2$ | HBr |
| 5 | $CH_3$ | $CH_3$ | $CH_3$ | $CH_3$ | $CH_3$ | O | HCl |
| 6 | $CH_3$ | $CH_3$ | $CH_3$ | $CH_3$ | $CH_3$ | O | HI |
| 7 | $CH_3$ | $CH_3$ | $C_2H_5$ | H | H | $CH_2$ | — |
| 8 | $CH_3$ | $CH_3$ | $C_2H_5$ | H | H | $CH_2$ | $(CO_2H)_2$ |
| 9 | $CH_3$ | $CH_3$ | $C_2H_5$ | $CH_3$ | $CH_3$ | O | — |
| 10 | $CH_3$ | $CH_3$ | $C_2H_5$ | $CH_3$ | $CH_3$ | O | $C_5H_{11}SO_3H$ |
| 11 | $CH_3$ | $C_2H_5$ | $C_2H_5$ | H | H | $CH_2$ | — |
| 12 | $CH_3$ | $C_2H_5$ | $C_2H_5$ | $CH_3$ | $CH_3$ | O | — |
| 13 | $C_2H_5$ | $C_2H_5$ | $C_2H_5$ | H | H | $CH_2$ | — |
| 14 | $C_2H_5$ | $C_2H_5$ | H | H | $CH_2$ | HBr | |
| 16 | $C_2H_5$ | $C_2H_5$ | $C_2H_5$ | $CH_3$ | $CH_3$ | O | $C_{12}H_{23}SO_3H$ |
| 17 | $C_2H_5$ | $C_2H_5$ | $C_2H_5$ | H | H | O | — |
| 18 | $n-C_3H_7$ | $CH_3$ | $CH_3$ | H | H | $CH_2$ | — |
| 19 | $n-C_3H_7$ | $CH_3$ | $CH_3$ | $CH_3$ | $CH_3$ | O | — |
| 20 | $n-C_4H_9$ | $CH_3$ | $CH_3$ | H | H | $CH_2$ | — |
| 21 | $n-C_4H_9$ | $CH_3$ | $CH_3$ | H | H | $CH_2$ | HCl |
| 23 | $n-C_4H_9$ | $CH_3$ | $CH_3$ | $CH_3$ | $CH_3$ | O | HBr |
| 24 | $n-C_4H_9$ | $CH_3$ | $CH_3$ | H | H | O | — |
| 26 | $i-C_4H_9$ | $CH_3$ | $CH_3$ | H | H | $CH_2$ | — |
| 27 | $i-C_4H_9$ | $CH_3$ | $CH_3$ | $CH_3$ | $CH_3$ | O | — |
| 28 | $t-C_4H_9$ | $CH_3$ | $CH_3$ | H | H | $CH_2$ | — |
| 29 | $t-C_4H_9$ | $CH_3$ | $CH_3$ | $CH_3$ | $CH_3$ | O | — |
| 30 | $t-C_4H_9$ | $CH_3$ | $CH_3$ | $CH_3$ | $CH_3$ | O | HCl |
| 32 | $CH_2Cl$ | $CH_3$ | $CH_3$ | $CH_3$ | $CH_3$ | O | HBr |
| 33 | $CH_2Cl$ | $CH_3$ | $CH_3$ | $CH_3$ | $CH_3$ | O | HCl |
| 34 | $CH_2Cl$ | $CH_3$ | $CH_3$ | H | H | $CH_2$ | — |
| 35 | $C_6H_{11}$ | $CH_3$ | $CH_3$ | H | H | $CH_2$ | — |
| 36 | $C_6H_{11}$ | $CH_3$ | $CH_3$ | $CH_3$ | $CH_3$ | O | — |
| 37 | $C_5H_9$ | $CH_3$ | $CH_3$ | $CH_3$ | $CH_3$ | O | — |
| 42 | $C_6H_5$ | $CH_3$ | $CH_3$ | $CH_3$ | $CH_3$ | O | HBr |
| 44 | $C_6H_5$ | $CH_3$ | $CH_3$ | H | H | O | HCl |
| 45 | $4-ClC_6H_5$ | $CH_3$ | $CH_3$ | H | H | $CH_2$ | — |
| 46 | $4-ClC_6H_5$ | $CH_3$ | $CH_3$ | $CH_3$ | $CH_3$ | O | — |
| 47 | $C_6H_5-CH_2$ | $CH_3$ | $CH_3$ | H | H | $CH_2$ | — |
| 48 | $C_6H_5CH_2$ | $CH_3$ | H | H | $CH_2$ | HCl | |
| 49 | $C_6H_5CH_2$ | $CH_3$ | $CH_3$ | $CH_3$ | $CH_3$ | O | — |
| 50 | $C_6H_5CH_2$ | $CH_3$ | $CH_3$ | $CH_3$ | $CH_3$ | O | $(CO_2H)_2$ |
| 51 | $CH_2=CH$ | $CH_3$ | $CH_3$ | $CH_3$ | $CH_3$ | O | — |
| 52 | $CH_3CH=CH_2$ | $CH_3$ | $CH_3$ | H | H | $CH_2$ | HBr |
| 53 | $C_6H_5$ | $C_6H_5$ | $CH_3$ | $CH_3$ | $CH_3$ | O | — |

The novel compounds, and their salts, have an excellent action on a broad spectrum of plant-pathogenic fungi, especially from the Ascomycetes and Basidiomycetes classes. Some of them have a systemic action and may be used as soil and foliar fungicides. They may also be employed for protecting materials.

The fungicidal compounds are of particular interest for combating a large number of fungi in various crops or their seed, especially wheat, rye, barley, oats, rice, Indian corn, cotton, soybeans, coffee, bananas, groundnuts, sugarcane, fruit, ornamentals in horticulture, and vegetables, such as cucumbers, beans and Cucurbitaceae.

The novel compounds are particularly suitable for combating the following diseases: *Erysiphe graminis* in cereals, *Erysiphe cichoriacearum* in Cucurbitaceae, *Podosphaera leucotricha* in apples, *Uncinula necator* in grapes, *Erysiphe polygoni* in beans, *Sphaerotheca pannosa* in roses, *Puccinia* species in cereals, *Rhizoctonia solani* in cotton, *Helminthosphorium* species in cereals, *Ustilago* species in cereals and sugarcane, *Rhynchosporium secale* in cereals, and *Venturia inaequalis* (apple scab).

The compounds are applied by spraying or dusting the plants, or treating the seed with the active ingredients. Application may be effected before or after infection of the plants or seed by the fungi.

The active ingredients of the invention can be converted into the conventional formulations, e.g. solutions, emulsions, suspensions, dusts, powders, pastes and granules. The form of application depends entirely on the purpose for which the agent is to be used; at all events, it should ensure a fine and uniform distribution of the active ingredients. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics. e.g. chlorobenzene, paraffins, e.g. petroleum fractions, alcohols, e.g. methanol and butanol, amines, e.g. ethanolamine, and dimethylformamide and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents generally contain from 0.1 to 95, preferably from 0.5 to 90, wt% of active ingredient. The application rates depend on the effect desired, and range from 0.1 to 3 kg of active ingredient per hectare, or more. The novel compounds may also be used as fungicidally effective components for protecting materials, e.g., in the form of oily wood preservatives for protecting timber against wood-destroying fungi. For instance the following wood-destroying fungi may be combated with the active ingredients according to the invention: *Merulius lacrimans, Coniophora puteana, Lentinus lepideus, Lenzites trabea, Trametes versicolor, Stereum hirsutum,* and *Fomos annosus.*

The novel active ingredients may be employed in formulations, such as solutions, emulsions, pastes and oil dispersions, or wound dressings. These formulations contain, for example, from 0.25 to 50% of active ingredient. The application rates depend on the effect desired, and range from 0.5 to 8 g of active ingredient per m$^2$ of wood surface to be protected, or from 50 to 4,000 g/m$^3$ of wood. Paints contain for instance from 0.5 to 2 wt% of active ingredient. To protect wood-base materials, the active ingredients may be added to the adhesive as an emulsion, or mixed with it, for example in amount of from 2 to 6 wt%.

The active ingredients are applied to the wood for example by painting, spraying, immersion, pressure impregnation, or diffusion.

The formulations and the ready-to-use products made therefrom, e.g., solutions, emulsions, suspensions, powders, dusts, pastes or granules, are applied in known manner—in crop protection for example by spraying, atomizing, dusting, scattering, seed-disinfecting, or watering.

Examples of such formulations are given below.

I. 90 parts by weight of compound 1 is mixed with 10 parts by weight of N-methyl-alpha-pyrrolidone. A mixture is obtained which is suitable for application in the form of very fine drops.

II. 10 parts by weight of compound 2 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil. By pouring the solution into water, an aqueous dispersion is obtained.

III. 20 parts by weight of compound 4 is dissolved in a mixture consisting of 60 parts by weight of cyclohexanone, 30 parts by weight of isobutanol, and 10 parts by weight of the adduct of 40 moles of ethylene oxide and 1 mole of castor oil. By pouring the solution into water and finely distributing it therein, an aqueous dispersion is obtained.

IV. 20 parts by weight of compound 15 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound 22 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound 2 is intimately mixed with 97 parts by weight of particulate kaolin. A dust is obtained containing 3% by weight of the active ingredient.

VII. 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 4 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound 2 is intimately mixed with 2 parts of the calcium salt of dodecylbenzenesulfonic acid, 8 parts of a fatty alcohol polyglycol ether, 2 parts of the sodium salt of phenolsulfonic acid-urea-formaldehyde condensate and 68 parts of a paraffinic mineral oil. A stable oily dispersion is obtained.

X. To prepare an oily wood preservative containing 1 wt% of active ingredient, 1 part (by weight) of compound 22 is dissolved, with slight heating, in 55 parts of a gasoline fraction rich in aromatics. Subsequently, 10 parts of an alkyd resin is added, and the mixture is made up to 100 parts by adding mineral spirit at room temperature.

Oily wood preservatives containing from 0.25 to 5 wt% of active ingredient 22 are prepared similarly.

If desired, water repellants may be added to the oily wood preservatives to give impregnating finishes. Examples of suitable substances are zinc stearate, aluminum stearate, and waxes. Further, particulate inorganic or organic pigments or oil-soluble dyes may be incorporated into the formulations to achieve color effects.

To protect wood against fungus attack, usually from 50 to 200 ml of the oily wood preservatives produced as in Example X is applied per m$^2$ of wood surface area by coating, spraying or dipping.

In these application forms, the agents according to the invention may also be mixed and applied with other active ingredients, e.g., herbicides, insecticides, growth regulators, other fungicides and fertilizers. When mixed with other fungicides, the spectrum of fungicidal action is in many cases increased.

The following list of fungicides, with which the compounds according to the invention may be combined, is intended to illustrate and not to restrict the combination possibilities.

Examples of fungicides which may be combined with the active ingredients according to the invention are as follows:
sulfur
dithiocarbamates and derivatives thereof, such as
ferric dimethyldithiocarbamate
zinc dimethyldithiocarbamate
zinc ethylenebisthiocarbamate
tetramethylthiuram disulfide
manganese-zinc ethylenediamine-bisdithiocarbamate
ammonia complex of zinc-(N,N'-ethylene)-bisdithiocarbamate and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate heterocyclic structures, such as
N-(1,1,2,2-tetrachloroethylthio)-tetrahydrophthalimide
N-trichloromethylthiotetrahydrophthalimide
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithi-(4,5-b)-quinoxaline
methyl 1-(butylcarbamoyl)-2-benzimidazole carbamate
4-(2-chlorophenylhydrazono)-3-methyl-5-isooxazolone
pyridine-2-thio-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene and various fungicides, such as
dodecylguanidine acetate
3-[2-(3,5-dimethyl-2-oxycyclohexyl)-2-hydroxyethyl]-glutarimide hexachlorobenzene
N-dichlorofluoromethylthio-N,N'-dimethyl-N-phenyl-sulfonic acid diamide
D,L-methyl-N-(2,6-dimethylphenyl)-N-(2-furoyl)-alanate
methyl D,L-N-(2,6-dimethylphenyl)-N-(2-methoxyacetyl)-alanate
diisopropyl 5-nitroisophthalate
2,5-dimethylfuran-3-carboxanilide
2-methylbenzoic acid anilide
2-iodobenzoic acid anilide
1-(3,4-dichloroanilino)-formylamino-2,2,2-trichloroethane
2,6-dimethyl-N-tridecylmorpholine and its salts
2,6-dimethyl-N-cyclododecylmorpholine and its salts
1-(1',2',4'-triazolyl-1')-1-(4'-chlorophenoxy)-3,3-dimethylbutan-2-one
1-(1',2',4'-triazolyl-1')-1-(4'-chlorophenoxy)-3,3-dimethylbutan-2-ol
N-(2,6-dimethylphenyl)-N-chloroacetyl-D,L-2-aminobutyrolactone
N-(n-propyl)-N-(2,4,6-trichlorophenoxyethyl)-N'-imidazolyl urea
N-cyclohexyl-N-methoxy-2,5-dimethylfuran-3-carboxamide 2,4,5-trimethylfuran-3-carboxanilide
5-methyl-5-vinyl-3-(3,5-dichlorophenyl)-2,4-dioxo-1,3-oxazolidine
5-methoxymethyl-5-methyl-3-(3,5-dichlorophenyl)-2,4-dioxo-1,3-oxazolidine
N-[3-(p-tert.-butylphenyl)-2-methylpropyl]-cis-2,6-dimethylmorpholine
N-formyl-N-morpholine-2,2,2-trichloroethyl acetal
1-[2-(2,4-dichlorophenyl)-4-ethyl-1,3-dioxolan-2-yl-ethyl]-1H-1,2,4-triazole
2-[2-(2,4-dichlorophenyl)-4-n-propyl-1,3-dioxolan-2-yl-ethyl]-1H-1,2,4-triazole.

For protecting wood, mixtures with the following compounds are particularly favorable:
organotin compounds, such as tributyltin oxide and tributyltin benozoate
methylene bis-thiocyanate
alkyl-dimethyl-benzylammonium chloride
cetyl-pyridinium chloride
chlorinated phenols, such as mercaptobenzothiazole, tetra and pentachlorophenol
tetrachloroisophthalic acid dinitrile
2-halobenzoic acid anilide
N-cyclohexyl-N-methoxy-2,5-dimethylfuran-3-carboxamide
2,4,5-trimethylfuran-3-carboxanilide
methyl benzimidazole-2-carbamate
2-thiocyanomethyl-thiobenzothiazole
copper naphthenate
copper-8-oxyquinoline
alkali metal salts of N-hydroxy-N-cyclohexyl-diazenium oxides
p-chlorophenyl-3-propargyl-formal
3-iodo-2-propynyl-butyl-carbamate
N-dichlorofluoromethylthio-N',N'-dimethyl-N-phenyl-sulfuric acid diamide.

The following experiments illustrate the fungicidal action. The following prior art compounds were used for comparison purposes:

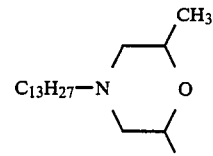

A

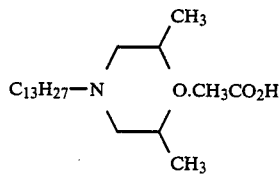

B

-continued

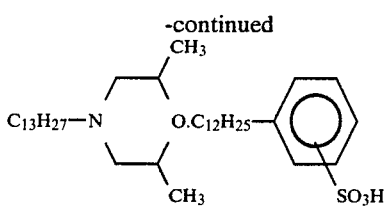

C

EXPERIMENT 1

Fungicidal action on wood-destroying fungi

To determine the activity on the wood-destroying fungi *Coniophora puteana* and *Trametes versicolor*, pine sapwood blocks measuring 50×25×15 mm were coated at a rate of 100 g/m² of wood surface with oily wood preservative formulations containing 1% of active ingredient. After the treated blocks had been stored for 4 weeks, they were placed, together with untreated blocks, in glass dishes containing the fungi *Coniophora puteana* or *Trametes versicolor* in a nutrient agar. The dishes were then incubated in an atmospheric laboratory at 22° C. and a relative humidity of 70%. After 3 months, the fungus mycelium attaching to the blocks was removed and the blocks were dried. The degree of wood destruction was then ascertained.

The results obtained show that for example compound 22, applied as a 1% formulation, had a good fungicidal action (e.g., 100%).

EXPERIMENT 2

Action on wheat mildew

Leaves of pot-grown wheat seedlings of the "Jubilar" variety were sprayed with aqueous liquors, the solids of which consisted of 80% (by weight) of active ingredient and 20% of emulsifier, and dusted, 24 hours after the sprayed-on layer had dried, with spores of wheat mildew (*Erysiphe graminis* var. tritici). The plants were then placed in a greenhouse at 20° to 22° C. and 75 to 80% relative humidity. The extent of mildew spread was determined after 7 days.

The results show that for instance compounds nos. 2, 4, 15 and 22, applied for example at rates of 0.025 or 0.006% spray liquors, had a better fungicidal action (e.g., 100%) than prior art active ingredients A, B and C (e.g., 90%).

EXPERIMENT 3

Action on leaf rust of wheat

Leaves of pot-grown wheat seedlings of the "Jubilar" variety were dusted with spores of rust (*Puccinia recondita*). The pots were then placed in a high humidity (90–95%) chamber at from 20° to 22° C. for 24 hours. During this time, the spores germinated and the germ tubes penetrated into the leaf tissue. The infected plants were then sprayed to run-off with aqueous liquors, the solids comprising 80% of active ingredient and 20% of emulsifier. After the spray coating had dried, the test plants were set up in a greenhouse at from 20° to 22° C. and from 65 to 70% relative humidity. After 8 days, the degree of development of the rust fungi on the leaves was determined.

The results show that for instance active ingredients 2, 4, 15 and 22, applied as 0.025% spray liquors, had a better fungicidal action (e.g., 100%) than prior art active ingredients A, B and C (e.g., 50%).

We claim:

1. A fungicidal composition containing a carrier and a fungicidally effective amount of an organosilyl compound of the formula

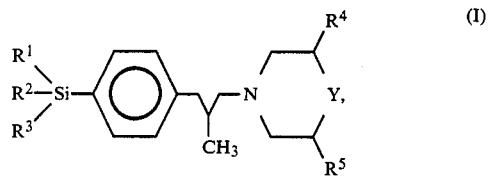

where $R^1$, $R^2$ and $R^3$ are identical or different and each is $C_1$–$C_{10}$-alkyl, $C_1$–$C_{10}$-alkyl-substituted by halogen, methoxy, ethoxy, dimethylamino, cyanononyl, methylthiomethyl, $C_2$–$C_4$-alkenyl, chloroallyl, methoxyallyl, $C_2$–$C_4$-alkynyl, cyclopropyl, cyclohexyl, cyclopentyl, cyclooctyl, methylcyclohexyl, dimethylcyclohexyl, phenyl, halophenyls, methoxyphenyl, tolyl, t-butylphenyl, methylthiophenyl or dimethylaminophenyl; $R^4$ and $R^5$ are identical or different and each is $C_1$–$C_5$-alkyl or hydrogen and Y is $CH_2$, oxygen, nitrogen or $C_1$–$C_2$-alkyl-substituted nitrogen, or a salt thereof.

2. The fungicidal composition of claim 1 wherein, in the organosilyl compound, $R^1$, $R^2$ and $R^3$ are $C_1$–$C_4$-alkyl, $R^4$ and $R^5$ are methyl or hydrogen, and Y is $CH_2$ or oxygen.

3. A process for combatting fungi which comprises applying to the materials to be protected a fungicidally effective amount of the composition of claim 1.

4. The process of claim 3, wherein the composition is applied to wood or wood-based materials, at an application rate of from 0.5 to 8 g of active ingredient per m² of wood surface to be protected.

5. The process of claim 3 wherein, in the organosilyl compound, $R^1$, $R^2$ and $R^3$ are $C_1$–$C_4$-alkyl, $R^4$ and $R^5$ are methyl or hydrogen, and Y is $CH_2$ or oxygen.

* * * * *